United States Patent
Mokelke et al.

(10) Patent No.: US 10,029,091 B2
(45) Date of Patent: Jul. 24, 2018

(54) APPARATUS FOR BARORECEPTOR STIMULATION THERAPY

(71) Applicant: Cardiac Pacemakers, Inc., St. Paul, MN (US)

(72) Inventors: Eric A. Mokelke, Flagstaff, AZ (US); Shantha Arcot-Krishnamurthy, Renton, WA (US); Brian Soltis, St. Paul, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 333 days.

(21) Appl. No.: 14/627,380

(22) Filed: Feb. 20, 2015

(65) Prior Publication Data

US 2015/0231391 A1    Aug. 20, 2015

Related U.S. Application Data

(60) Provisional application No. 61/942,491, filed on Feb. 20, 2014.

(51) Int. Cl.
*A61N 1/05* (2006.01)
*A61N 1/36* (2006.01)

(52) U.S. Cl.
CPC ........ *A61N 1/0558* (2013.01); *A61N 1/36114* (2013.01); *A61N 1/36117* (2013.01)

(58) Field of Classification Search
CPC .............. A61N 1/0558; A61N 1/36114; A61N 1/36117
See application file for complete search history.

(56) References Cited

U.S. PATENT DOCUMENTS

| 5,476,493 | A |   | 12/1995 | Muff |
| 5,674,272 | A | * | 10/1997 | Bush ...................... A61N 1/056 |
|           |   |   |         | 600/374 |

(Continued)

FOREIGN PATENT DOCUMENTS

| CN | 101244315 A | 8/2008 |
| CN | 102438696 A | 5/2012 |

(Continued)

OTHER PUBLICATIONS

International Preliminary Report on Patentability issued in PCT/US2015/036526, dated Dec. 20, 2016, 8 pages.

(Continued)

*Primary Examiner* — Amanda Hulbert
(74) *Attorney, Agent, or Firm* — Faegre Baker Daniels LLP

(57) ABSTRACT

A medical apparatus comprising an implantable lead and a stylet configured for stimulation of a target region of a patient's nervous system is described. The lead includes a generally tubular lead body, a conductor, and an electrode assembly. The generally tubular lead body has a stylet lumen and a conductor lumen extending through the proximal and distal ends of the lead body. The conductor is enclosed within the conductor lumen. The electrode assembly extends from the distal end of the lead body. The electrode assembly includes a flexible polymeric carrier and an electrode on the carrier and electrically coupled to the conductor. The stylet is sized and shaped to be receivable within the stylet lumen and configured to stiffen and support the lead body. The distal portion of the stylet includes a bend having a predetermined angle of incidence relative to the proximal portion of the stylet.

16 Claims, 5 Drawing Sheets

(56) References Cited

U.S. PATENT DOCUMENTS

| | | | |
|---|---|---|---|
| 6,055,448 A | 4/2000 | Anderson et al. | |
| 6,314,315 B1 | 11/2001 | Hung et al. | |
| 6,564,079 B1 | 5/2003 | Cory et al. | |
| 6,575,991 B1 | 6/2003 | Chesbrough et al. | |
| 6,909,920 B2 * | 6/2005 | Lokhoff | A61N 1/057 607/119 |
| 6,985,774 B2 | 1/2006 | Kieval et al. | |
| 7,006,875 B1 | 2/2006 | Kuzma et al. | |
| 7,015,061 B2 | 3/2006 | Lu et al. | |
| 7,337,005 B2 | 2/2008 | Kim et al. | |
| 7,445,953 B2 | 11/2008 | Lu et al. | |
| 7,502,650 B2 | 3/2009 | Kieval | |
| 7,616,997 B2 | 11/2009 | Kieval et al. | |
| 7,813,812 B2 | 10/2010 | Kieval et al. | |
| 8,126,560 B2 | 2/2012 | Scheiner et al. | |
| 8,175,705 B2 | 5/2012 | Libbus | |
| 8,571,664 B2 | 10/2013 | Anderson et al. | |
| 8,774,941 B2 * | 7/2014 | Pianca | A61N 1/0553 607/117 |
| 8,901,268 B2 | 12/2014 | Krishnamoorthy et al. | |
| 8,948,872 B2 | 2/2015 | Shuros et al. | |
| 9,345,877 B2 | 5/2016 | Pignato et al. | |
| 9,795,778 B2 | 10/2017 | Mokelke et al. | |
| 9,839,785 B2 | 12/2017 | Mokelke et al. | |
| 2002/0095080 A1 | 7/2002 | Cory et al. | |
| 2003/0187490 A1 | 10/2003 | Gliner | |
| 2004/0176759 A1 | 9/2004 | Krishnamurthy et al. | |
| 2005/0085884 A1 | 4/2005 | O'Brien et al. | |
| 2005/0096710 A1 | 5/2005 | Kieval | |
| 2005/0154418 A1 | 7/2005 | Kieval et al. | |
| 2005/0182456 A1 | 8/2005 | Ziobro et al. | |
| 2006/0085049 A1 | 4/2006 | Cory et al. | |
| 2006/0276704 A1 | 12/2006 | McGinnis et al. | |
| 2007/0021792 A1 | 1/2007 | Kieval et al. | |
| 2007/0027512 A1 | 2/2007 | Chan et al. | |
| 2007/0161912 A1 | 7/2007 | Zhang et al. | |
| 2007/0208391 A1 | 9/2007 | Wahlstrand et al. | |
| 2007/0213795 A1 * | 9/2007 | Bradley | A61N 1/0558 607/116 |
| 2008/0004673 A1 | 1/2008 | Rossing et al. | |
| 2008/0046051 A1 | 2/2008 | Skubitz et al. | |
| 2008/0046054 A1 | 2/2008 | Hjelle et al. | |
| 2008/0147146 A1 | 6/2008 | Wahlgren et al. | |
| 2009/0132002 A1 | 5/2009 | Kieval | |
| 2009/0143837 A1 | 6/2009 | Rossing et al. | |
| 2009/0234418 A1 | 9/2009 | Kieval et al. | |
| 2010/0152826 A1 | 6/2010 | Tanabe et al. | |
| 2010/0298698 A1 | 11/2010 | Burbank et al. | |
| 2010/0324641 A1 | 12/2010 | Skubitz et al. | |
| 2011/0257716 A1 | 10/2011 | Tiedtke | |
| 2012/0271389 A1 | 10/2012 | Cates et al. | |
| 2013/0018247 A1 | 1/2013 | Glenn et al. | |
| 2013/0150940 A1 | 6/2013 | Wilson et al. | |
| 2013/0172920 A1 | 7/2013 | Euteneuer et al. | |
| 2014/0276037 A1 | 9/2014 | Johnson et al. | |
| 2015/0018918 A1 | 1/2015 | Mokelke et al. | |
| 2015/0165215 A1 | 6/2015 | Mokelke et al. | |
| 2015/0231391 A1 | 8/2015 | Mokelke | |
| 2015/0366465 A1 | 12/2015 | De Kock et al. | |
| 2015/0366467 A1 | 12/2015 | De Kock et al. | |
| 2016/0059005 A1 | 3/2016 | De Kock et al. | |
| 2016/0074650 A1 | 3/2016 | De Kock et al. | |
| 2017/0325865 A1 | 11/2017 | Euteneuer et al. | |

FOREIGN PATENT DOCUMENTS

| | | |
|---|---|---|
| EP | 2108398 B1 | 10/2009 |
| EP | 1487535 B1 | 6/2012 |
| JP | 2004526471 A | 9/2004 |
| JP | 2009519050 A | 5/2009 |
| JP | 2009532102 A2 | 9/2009 |
| JP | 2009532185 A | 9/2009 |
| JP | 2010505465 A | 2/2010 |
| JP | 2012130579 A | 7/2012 |
| JP | 2013541390 A | 11/2013 |
| KR | 20120053090 A | 5/2012 |
| WO | 2002026314 A1 | 4/2002 |
| WO | WO0226314 A1 | 4/2002 |
| WO | 2007118090 A2 | 10/2007 |
| WO | 2015195980 A1 | 12/2015 |
| WO | 2015195982 A2 | 12/2015 |

OTHER PUBLICATIONS

International Preliminary Report on Patentability issued in PCT/US2015/036528, dated Dec. 20, 2016, 9 pages.
International Preliminary Report on Patentability issued in PCT/US2014/046008, dated Jan. 28, 2016, 8 pages.
International Search Report and Written Opinion issued in PCT/US2015/036526, dated Oct. 26, 2015, 12 pages.
International Search Report and Written Opinion Issued in PCT/US2015/036528, dated Jan. 19, 2016, 15 pages.
International Search Report and Written Opinion issued in PCT/US2015/050303, dated Jan. 14, 2016, 12 pages.
Invitation to Pay Additional Fees and, Where Applicable, Protest Fee issued in PCT/US2015/036528, dated Oct. 28, 2015, 6 pages.
International Search Report and Written Opinion] issued in PCT/US2014/046008, dated Oct. 1, 2014, 12 pages.
International Preliminary Report on Patentability issued in PCT/US2015050303, dated Mar. 30, 2017, 8 pages.

* cited by examiner

APPARATUS FOR BARORECEPTOR STIMULATION THERAPY

CROSS-REFERENCE TO RELATED APPLICATION

This application claims priority to Provisional Application No. 61/942,491, filed Feb. 20, 2014, which is herein incorporated by reference in its entirety.

TECHNICAL FIELD

The present invention relates to medical apparatuses for stimulating a target region in a patient's body. More particularly, the present disclosure is related to apparatuses, systems and methods for mapping and stimulating excitable tissue such as neural tissue of the autonomic nervous system, particularly the regions near the carotid artery bifurcation, which includes the carotid sinus and carotid body.

BACKGROUND

Research suggests that electrical stimulation of neural tissue is effective in transmitting or inhibiting neural signals (action potentials) to the end organs or the central regions of the brain. Thus, electrical stimulation of neural tissue can be used to modulate neural activity that may alter end organ function or reflex activity after being integrated with other input signals in the brain. One example of such a reflex pathway is the electrical stimulation of the baroreceptors on the carotid sinus or the carotid body which can alter blood pressure, heart rate, and respiration. Another example is electrical stimulation of the vagal nerve which has been shown to alter heart rate and respiration. In a specific instance, electrical stimulation of the baroreceptors in the carotid sinus has been shown to reduce blood pressure, as well as the number of arrhythmic events. The baroreceptors on the carotid sinus can be electrically stimulated temporarily or permanently by placing electrodes on or near the carotid sinus, within which the baroreceptors are distributed. The carotid body, which is situated near the carotid sinus can be stimulated to inhibit neural traffic to the brain which may reduce the amount of overall sympathetic activity. To locate optimal electrode placement positions for these types of stimulation, one way to identify the treatment location is to perform electrical mapping of the carotid sinus or the bifurcation area. Hence, there is a need to develop improved tools and techniques for facilitating the mapping of the baroreceptors and/or the carotid body located within or near the carotid sinus for delivery of chronic electrical therapy.

SUMMARY

In Example 1, an implantable lead for stimulating the baroreceptors located within a carotid sinus of a patient, the lead comprising a generally tubular body, a conductor and an electrode assembly. The lead body has a proximal end, an opposite distal end, and further includes a first tubular member having a stylet lumen extending therethrough, and a second tubular member coupled to the first tubular member and having a conductor lumen extending therethrough. The stylet and conductor lumens extend through the proximal and distal ends of the tubular lead body. The conductor is enclosed within the conductor lumen. The electrode assembly extends from the distal end of the lead body.

In Example 2, the implantable lead of Example 1, wherein the first tubular member is separable from the second tubular member.

In Example 3, the implantable lead of either of Examples 1 or 2, wherein the first tubular member and the second tubular member are coupled together by a separable interface therebetween.

In Example 4, the implantable lead of any of Examples 1-3, wherein the separable interface is a tearable interface configured to facilitate separation of the first and second tubular members.

In Example 5, the implantable lead of any of Examples 1-4, wherein the electrode assembly includes a flexible polymeric carrier, and an electrode on the carrier and electrically coupled to the conductor.

In Example 6, the medical apparatus of any of Examples 1-5, wherein the conductor lumen and the stylet lumen are situated in a side-by-side arrangement.

In Example 7, the medical apparatus of any of Examples 5-6, further comprising a second conductor enclosed within a second conductor lumen.

In Example 8, the medical apparatus of Example 7, further comprising a second electrode electrically coupled to the second conductor.

In Example 9, the medical apparatus of any of Examples 1-8, wherein the lead body includes a first tubular member, the stylet lumen extending through the first tubular member, wherein the first tubular member has a circular opening at a distal end of the first tubular member.

In Example 10, a medical apparatus, comprising an implantable lead according to any of Examples 1-9, and a stylet sized and shaped to be receivable within the stylet lumen and configured to stiffen and support the lead body, wherein the stylet includes a proximal portion and a distal portion, the distal portion including a bend having a predetermined angle of incidence relative to the proximal portion of the stylet.

In Example 11, the medical apparatus of Example 10, further comprising a temporary anchoring element coupled to the distal end of the stylet.

In Example 12, the medical apparatus of either of Examples 10 or 11, wherein the temporary anchoring element comprises a barb configured to engage with patient tissue and is configured to extend from and retract to the distal end of the stylet.

In Example 13, the medical apparatus of Example 12, wherein the barb comprises a tip portion configured to engage with the patient tissue.

In Example 14, the medical apparatus of Example 10, wherein the temporary anchoring element comprises a fixation helix with a sharp tip portion that is configured to be extendable from and retractable with respect to the distal end of the stylet when the stylet is rotated relative to the lead body.

In Example 15, the medical apparatus of any of Examples 10-14, wherein the lead body includes a first tubular member, the stylet lumen extending through the first tubular member, wherein the first tubular member has a circular opening at a distal end of the first tubular member and wherein the stylet is configured to extend past and retract into the first tubular member through the circular opening.

In Example 16, a medical apparatus comprising an implantable lead for stimulation of a target region of a patient's nervous system, and a stylet. The lead includes a lead body, a conductor, and an electrode assembly. The lead body is generally tubular and has a proximal end, an opposite distal end, a stylet lumen and a conductor lumen, the stylet and conductor lumens extending through the proximal and distal ends of the tubular lead body. The conductor is enclosed within the conductor lumen. The electrode assembly extends from the distal end of the lead body, the electrode assembly including a flexible polymeric carrier, and an electrode on the carrier and electrically coupled to the conductor. The stylet is sized and shaped to be receivable within the stylet lumen and configured to stiffen and support the lead body, wherein the stylet includes a proximal portion and a distal portion, the distal portion including a bend having a predetermined angle of incidence relative to the proximal portion of the stylet.

In Example 17, the medical apparatus of Example 16, wherein the lead body includes a first tubular member and a second tubular member secured to the first tubular member, the stylet lumen extending through the first tubular member, wherein the first tubular member is separable from the second tubular member.

In Example 18, the medical apparatus of either of Examples 16 or 17, wherein the lead body further comprises a separable interface between the first tubular member and the second tubular member, wherein the stylet is detachable from the lead body at the separable interface by removing the first tubular member along the separable interface.

In Example 19, the medical apparatus of any of Examples 16-18, further comprising a temporary anchoring element coupled to the distal end of the stylet.

In Example 20, the medical apparatus of Example 19, wherein the temporary anchoring element comprises a barb configured to engage with patient tissue and is configured to extend from and retract to the distal end of the stylet.

In Example 21, the medical apparatus of Example 20, wherein the barb comprises a tip portion configured to engage with the patient tissue.

In Example 22, the medical apparatus of Example 20, wherein the temporary anchoring element comprises a fixation helix with a sharp tip portion that is configured to be extendable from and retractable with respect to the distal end of the stylet when the stylet is rotated relative to the lead body.

In Example 23, the medical apparatus of any of Examples 16-22, wherein the conductor lumen and the stylet lumen are situated in a side-by-side arrangement.

In Example 24, the medical apparatus of any of Examples 16-23, further comprising a second conductor enclosed within a second conductor lumen.

In Example 25, the medical apparatus of any of Examples 16-24, further comprising a second electrode electrically coupled to the second conductor.

In Example 26, the medical apparatus of any of Examples 16-25, wherein the lead body includes a first tubular member, the stylet lumen extending through the first tubular member, wherein the first tubular member has a circular opening at a distal end of the first tubular member and wherein the stylet is configured to extend past and retract into the first tubular member through the circular opening.

In Example 27, the medical apparatus of any of Examples 16-26, wherein the carrier is composed of a silicone-based material.

In Example 28, an implantable lead for stimulating the baroreceptors located within a carotid sinus of a patient, the lead comprising a lead body, a conductor, and an electrode assembly. The lead body is generally tubular and has a proximal end, an opposite distal end, and further includes a first tubular member having a stylet lumen extending therethrough, and a second tubular member coupled to the first tubular member and having a conductor lumen extending therethrough. The stylet and conductor lumens extend through the proximal and distal ends of the tubular lead body. The conductor is enclosed within the conductor lumen. The electrode assembly extends from the distal end of the lead body, and includes a flexible polymeric carrier, and an electrode on the carrier and electrically coupled to the conductor. The first tubular member is separable from the second tubular member.

In Example 29, the implantable lead of Example 28, wherein the first tubular member and the second tubular member are coupled together by a separable interface therebetween.

In Example 30, the implantable lead of Example 29, wherein the separable interface is a tearable interface configured to facilitate separation of the first and second tubular members.

In Example 31, a method of implanting an implantable lead for stimulation of the baroreceptors located within a carotid sinus of a patient, the method comprising advancing a stylet into a stylet lumen of a lead body of the implantable lead. The lead body comprises the stylet lumen and a conductor lumen, wherein a conductor is enclosed within the conductor lumen, and wherein the stylet is sized and shaped to be receivable within the stylet lumen, the stylet including a bend defining a distal portion of the stylet having a predetermined angle of incidence relative to a proximal portion of the stylet proximal to the bend. The method further comprises positioning an electrode of the implantable lead proximate to a target physiological region of a patient by using the stylet to stiffen and support the lead body, wherein the electrode is electrically coupled to the conductor at a distal end of the conductor.

In Example 32, the method of Example 31, further comprising rotating the stylet to expose a temporary anchoring element.

In Example 33, the method of Example 32, further comprising engaging the temporary anchoring element with patient tissue.

In Example 34, the method of any of examples 31-33, further comprising securing the electrode to the patient, and removing the stylet from the medical apparatus upon securing the electrode to the patient.

In Example 35, the method of Example 34, wherein removing the stylet from the medical apparatus comprises removing a first tubular member defining the stylet lumen from the medical apparatus, wherein the stylet remains enclosed within the first tubular member while removing the first tubular member.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
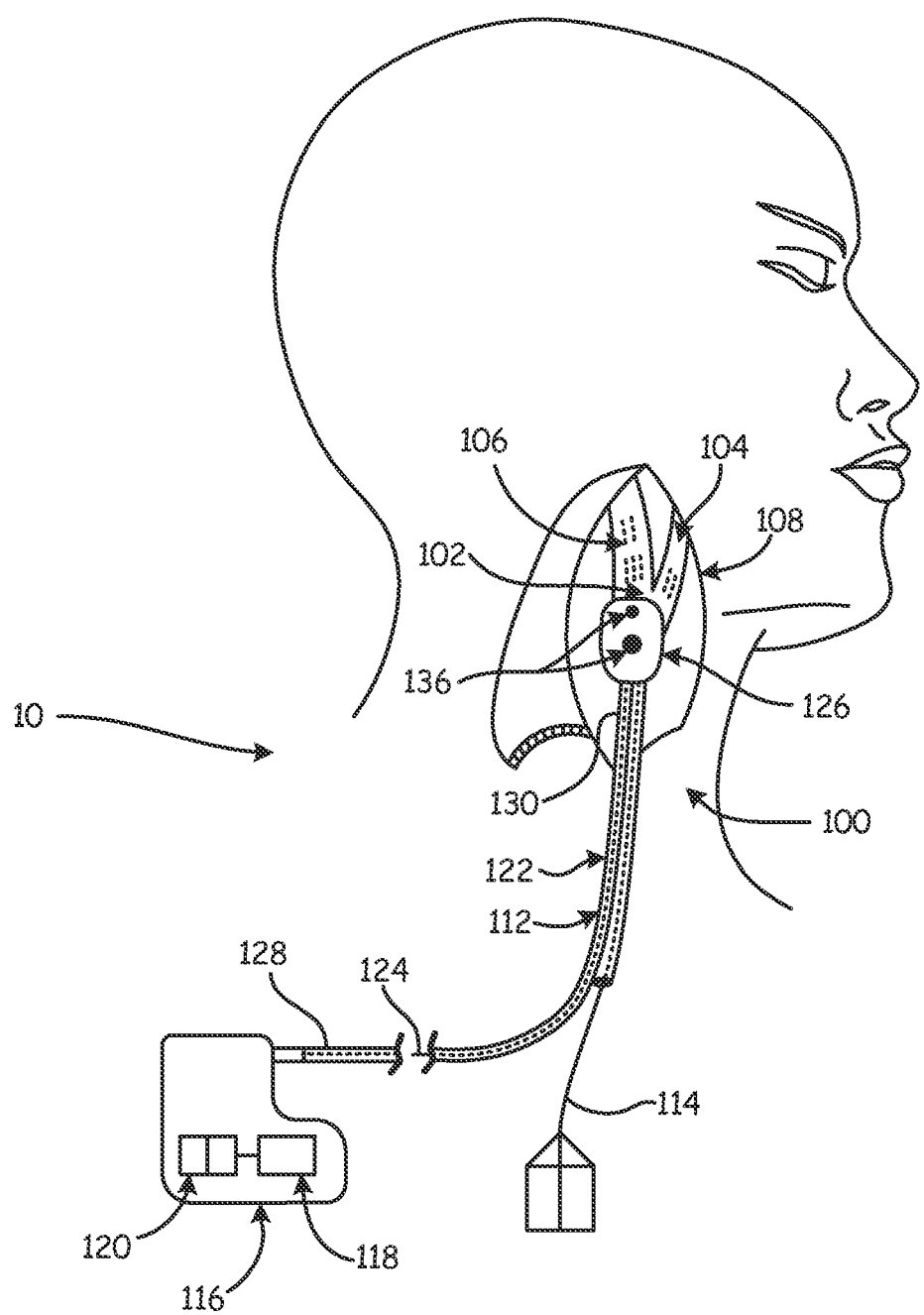
FIG. 1 is a schematic illustration of a medical apparatus according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration showing an exemplary stimulation system 10 including a medical apparatus 100. In the various embodiments, the stimulation system 10 is configured to sense and stimulate a target physiological region. In some embodiments, the target physiological region may be the vascular tissue and/or the carotid sinus of a patient, which consists of multiple layers of fascia wrapping the common carotid artery 102, the internal carotid artery 104, and the external carotid artery 106. The carotid sinus may be accessed by an incision 108 in the fascia or other tissue of a patient 110. Generally speaking, the internal carotid artery 104 may include a number of baroreceptors, which an operator may seek to target during a therapy procedure. To determine an optimal location at which to place one or more electrodes used in such a therapy procedure, the operator may first map the target physiological region.

In the illustrated embodiment, the medical apparatus 100 includes an implantable lead 112 and a stylet 114 usable by the implanting physician in identifying the optimal implantation location and position for the implantable lead 112. As shown, the implantable lead 112 can be mechanically and electrically coupled to a pulse generator 116 which is configured to work in conjunction with the implantable lead 112 to accomplish various operations, such as mapping the target region, producing electric signals for stimulating the target region, or the like. To accomplish such operations, the pulse generator 116 includes a power source 118 and electronic circuitry 120. In one embodiment, the power source 118 includes a battery that can provide power to the implantable lead 112 for its operations. Those skilled in the art will understand that any suitable power source 118 may also be contemplated. The electronic circuitry 120 may include various electronic components for mapping the target region and regulating stimulation signals to be delivered to the target region. Exemplary components of the electronic circuitry 120 may include processing circuitry, telemetry circuitry, memory, or the like.

Figure 2:
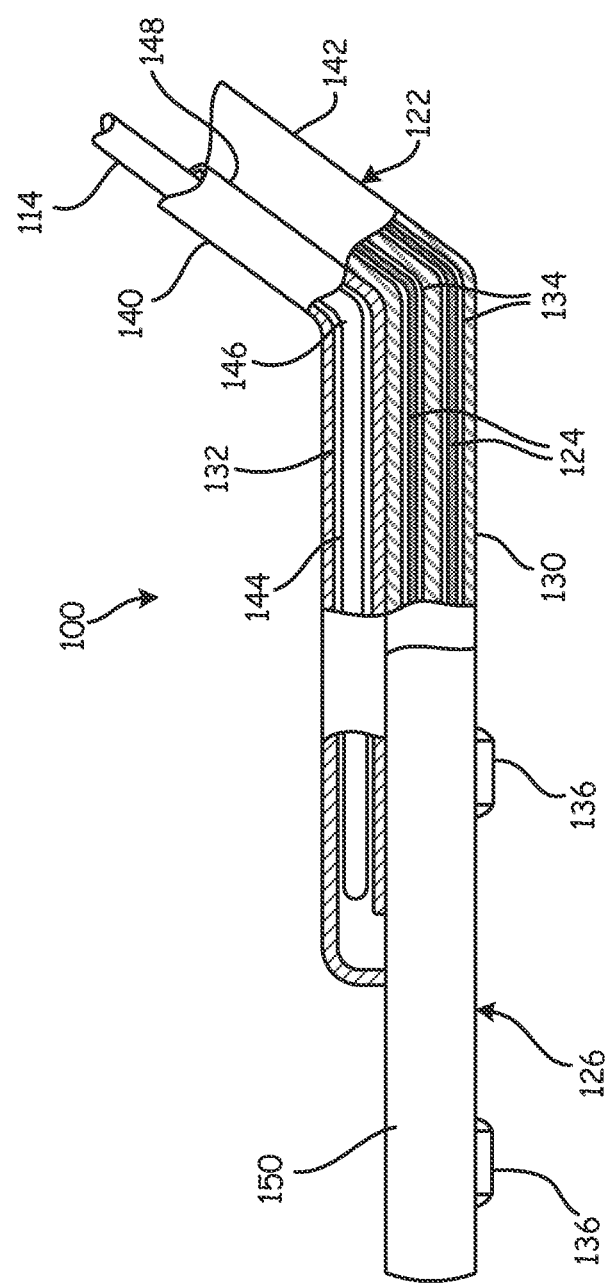
FIG. 2 is a schematic illustration of the medical apparatus of FIG. 1 including a lead according to one embodiment.

FIG. 2 is a partial cut-away schematic illustration of the medical apparatus 100 according to one embodiment. Referring to FIGS. 1 and 2, the implantable lead 112 includes a lead body 122, one or more conductors 124, and an electrode assembly 126. In the various embodiments, the lead body 122 is generally tubular and includes a proximal end 128, a distal end 130, a stylet lumen 132, and a plurality of conductor lumens 134 extending from the proximal end 128 to the distal end 130 of the lead body 122. The stylet lumen 132 is structured to receive the stylet 114, which provides desired stiffness and support to the lead body 122 in order to stabilize the lead 112 during mapping of the target physiological region. In such a manner, the stylet 114 facilitates accurate positioning of the lead body 122 adjacent the target region. Each conductor lumen 134 is configured to receive a conductor 124, which is capable of electrically coupling the electrode assembly 126 with the pulse generator 116. In particular, the electrode assembly 126 includes one or more electrodes 136 that can be electrically coupled to the pulse generator 116 via one or more conductors 124. Such electrical coupling enables the electrodes 136 in mapping the target region comprising baroreceptors. Once the electrodes 136 are positioned at the target region, electrical signal from the pulse generator 116 may be delivered to the electrodes 136 to electrically stimulate the target region.

For efficient mapping as well as stimulation, the electrode assembly 126 and the target region (surface of the carotid sinus) need to be maintained in substantial contact with each other. In various embodiments, an operator may monitor impedance values to assess the contact between the surface of the carotid sinus and the electrode assembly 126. An optimum pressure may be applied by manipulating the stylet 114 to maintain contact as well as avoid undesired stimulation of baroreceptors.

As further shown in FIG. 2, in one embodiment, the lead body 122 includes a first tubular member 140 and a second tubular member 142. In the illustrated embodiment, the first tubular member 140 defines the stylet lumen 132 extending longitudinally along a length of the first tubular member 140 and is configured to receive the stylet 114. In the illustrated embodiment, the first tubular member 140 and the stylet lumen 132 are configured to have a circular cross-section. However, any other suitable cross-section such as but not limited to triangular, oval, rectangular, or the like may also be contemplated. The cross-sectional shape and size of the first tubular member 140 can be designed so as to facilitate easy insertion and removal of the stylet 114.

The stylet 114 includes a proximal portion (not shown) and a distal portion 144 and is sized and shaped to be inserted into the stylet lumen 132. In general, the stylet 114 is configured to stabilize the lead 112 during the mapping and/or stimulation procedures by providing stiffness and support to the lead body 122. The distal portion 144 of the stylet 114 includes a bend 146 having a predetermined angle of incidence relative to the proximal portion of the stylet 114. The bend 146 enables the lead 112 to be suitably placed at the target region through the incision 108. In some embodiments, the angle of incidence may be an obtuse angle selected by physician. In various embodiments, this angle of incidence may range, for example, from just over 90 degrees to about 170 degrees, depending on the physician's preference.

As further shown, the second tubular member 142 defines the conductor lumens 134 extending longitudinally along a length of the second tubular member 142. The second tubular member 142 and the conductor lumen 134 may have a circular, triangular, rectangular, elliptical, ovular cross-section, or the like. In various embodiments, the conductor lumen 134 is configured to receive more than one conductor 124. The conductor 124 disposed in the conductor lumen 134 is physically and electrically coupled to the electrode assembly 126, such that each conductor 124 is electrically coupled to one of the electrodes 136.

In an embodiment, the first tubular member 140 is secured to the second tubular member 142 such that the two tubular members 140, 142 are separable from one another. For instance, the stylet 114 disposed in the first tubular member 140 may be required only at the time of mapping. Once the mapping of target region is done and the lead 112 is fixed, an operator may need to remove the stylet 114 from the lead body 122. To accomplish this, the lead body 122 includes a separable interface 148 disposed between the first tubular member 140 and second tubular member 142, where the first and second tubular members 140, 142 be separated from one another at the separable interface 148. As a result, the stylet 114 is removed from the lead body 122 by removing the first tubular member 140 along the separable interface 148.

In some embodiments, the first tubular member 140 and the second tubular member 142 can be made of a continuous single tubular member, e.g., monolithically formed unitary structure. To form such a unitary structure, a tube may be crimped along its longitudinal length dividing the tube into two tubular members such as first tubular member 140 and the second tubular member 142, and the interface between the tubular members 140, 142 can be fused (e.g., by heating). In such scenario, the crimped surface may form the separable interface 148 along which the two tubular members 140, 142 can be separated. In other embodiments, the first and second tubular members 140, 142 can be molded or co-extruded as a unitary tubular member. In other embodiments, the first tubular member 140 and the second tubular member 142 may be discrete and coupled using a suitable technique known in the art. Exemplary techniques include welding, soldering, heat bonding, stamping, or the like. Generally, any suitable technique that can couple the first tubular member 140 to the second tubular member 142 while forming a separable interface 148 between them can be contemplated.

The electrode assembly 126 is disposed at the distal end 130 of the lead body 122 and includes a flexible polymeric carrier 150 and the electrodes 136 disposed on the carrier 150. The carrier 150 holds and supports the electrodes 136 and keeps the electrode assembly 126 intact. In various embodiments, the carrier 150 may be formed using silicone-based material. Other suitable materials used to form the carrier 150 include, but are not limited to, polyurethane, high density polyethylene, polyvinyl chloride, or the like.

As shown, in the illustrated embodiment, the electrode assembly 126 includes two electrodes 136 disposed on the carrier 150. However, it is contemplated that the electrode assembly 126 may include any suitable number of electrodes 136. In some embodiments, the electrodes 136 are configured to map as well as stimulate the target region. However, in some other embodiments, the electrode assembly 126 may include one or more additional elements sensors, or the like, that can facilitate mapping of the target region to detect the location of baroreceptors, for example.

The electrode 136 may be formed using a suitable conducting biocompatible material, such as, but not limited to, titanium, platinum, gold, silver, or the like. In various embodiments, one or more electrodes 136 include a circular pad-like component sized to partially or wholly cover the carotid sinus area.

In one embodiment, the electrodes 136 are configured to map the target region to locate the baroreceptors for stimulation. The electrodes 136 can be used to stimulate the tissue at the potential target physiological region, and the response of the tissue is measured with respect to the stimulation provided by the electrodes 136. The measured response helps the operator locate or determine proximity to the baroreceptors. Once the baroreceptors are located and the physician determines that the implantation location and position is suitable, the stylet 114 can be removed and the first tubular member 140 can be separated from the lead body 122 resulting in implantation of the lead 112 at the target region.

Figure 3:
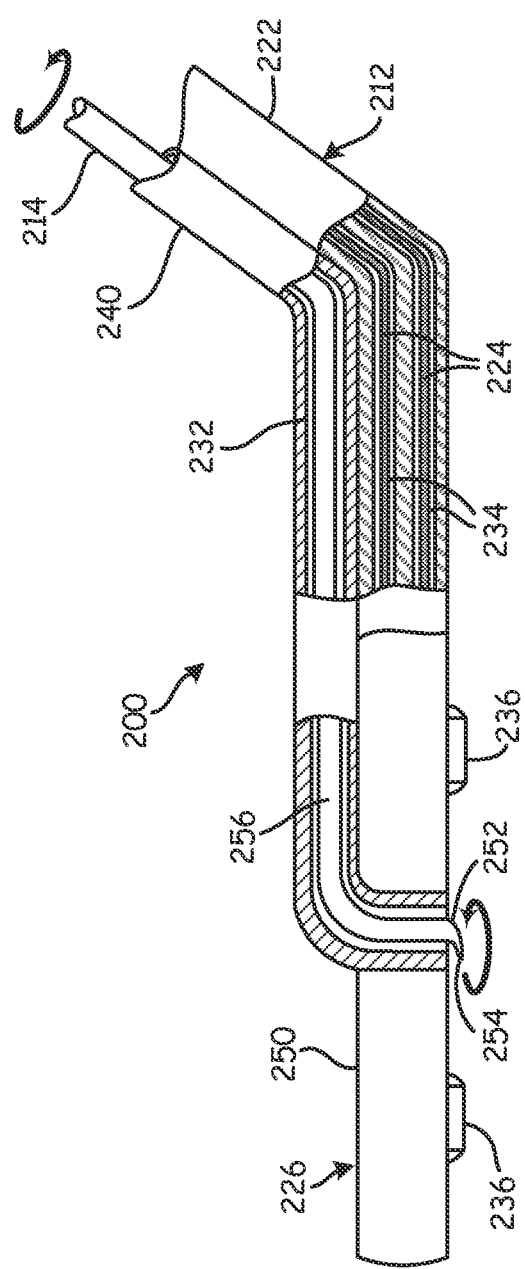
FIGS. 3-4 are schematic illustrations of the medical apparatus of FIG. 1 including a lead according to various embodiments.

FIG. 3 is a partial cut-away schematic illustration of a medical apparatus 200 according to one embodiment. The medical apparatus 200 includes an implantable lead 212 (including a lead body 222, two conductors 224, and an electrode assembly 226) and a stylet. The lead body 222, conductors 224, and electrode assembly 226 (including electrodes 236, and a carrier 250) can be configured in substantially the same manner as the corresponding components of the medical apparatus 100 shown in FIG. 2, except as described below. The lead body 222 includes a first tubular member 240 defining a stylet lumen 232 attached to the second tubular member defining the conductor lumen 234. The stylet lumen 232 is configured to receive a stylet 214 having a temporary anchoring element 252 disposed at its distal end 256.

The temporary anchoring element 252 is configured to be engaged with the patient tissue proximate a target region. In various embodiments, the temporary anchoring element 252 is a barb that includes a tip portion 254 configured to engage with the patient tissue. The barb may extend out of an opening in the carrier 250 to engage with the tissue, where the opening is formed along a distal portion of the first tubular member. In one embodiment, there is no pre-formed opening in the carrier 250, and the tip portion 254 is configured to pierce the material of the carrier 250 so as to expose the tip portion 254 so that it can engage the tissue. In other embodiments, the temporary anchoring element 252 can be a pin, needle, hook or the like. In some embodiments, the temporary anchoring element 252 includes a sharp tip portion 254 that operates to engage tissue when rotated to secure the stylet 214 in position.

In particular, the temporary anchoring element 252 provides stability to the lead 212 while positioning, maintaining, or re-positioning of the electrode assembly 226 and minimize inadvertent motion of the electrode assembly 226. Depending on the duration of mapping procedure, the temporary anchoring element 252 can be removed once the mapping at a particular location is completed.

In some embodiments, the temporary anchoring element 252 may be extended from and retracted into the distal end 256 of the stylet 214. In various embodiments, the stylet 214 may be turned or rotated in clockwise direction to extend the temporary anchoring element 252 from the distal end of the stylet (as shown in the enlarged view FIG. 3) so that the tip portion 254 may engage with the patient tissue. To retract the temporary anchoring element 252 from the tissue, the stylet 214 may then be rotated or turned in counter-clockwise direction and pulled in the proximal direction relative to the lead body 222. In such scenarios, the temporary anchoring element 252 may be in the form of a fixation helix (similar to a cork screw) extending helically from the distal end 256 of the stylet 214.

Figure 4:
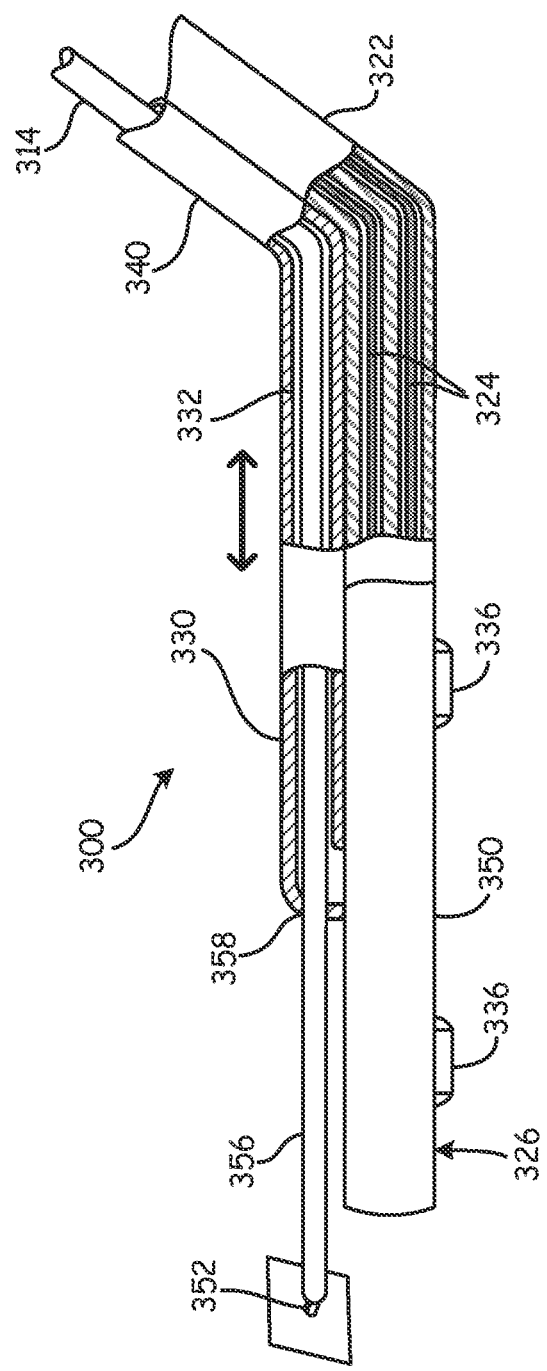

FIG. 4 is a partial cut-away schematic illustration of the medical apparatus 300 according to one embodiment. The medical apparatus 300 includes a lead 312 having a lead body 322, a pair of conductors 324, and an electrode assembly 326. The lead body 322, the conductors 324, and the electrode assembly 326 can be configured in substantially the same or in an identical manner as the corresponding components of the medical apparatus 100 shown in FIG. 2. A stylet 314 extends from a distal end 330 of the lead body 322 via an opening 358 at a distal end of the first tubular member 340. In one configuration, the user may extend the stylet 314 past the distal end of the first tubular member 340 (as shown) or retract the stylet 314 within the first tubular member 340 in another configuration.

A distal end 356 of the stylet 314 includes a temporary anchoring element 352 that can be attached to patient tissue at a location proximate a target region. After anchoring the distal end 356 of the stylet 314 via the temporary anchoring element 352, the lead 312 including the carrier 350 and the electrodes 336 can be moved from one location to other location by sliding the lead body 322 relative to the stylet 314. Thus, an over-the-wire system may be obtained. Anchoring may provide additional stability to the medical apparatus 300 and also guide positioning of the lead 312 along a linear path in the target region (such as target region). Re-positioning of the lead 312 may be particularly helpful during mapping of the target region. During mapping, if an anchoring point does not yield electrode positions with desired proximity to baroreceptors, then the user may detach the stylet 314 by retracting the temporary anchoring element 352 and re-attaching it at a new location.

Figure 5:
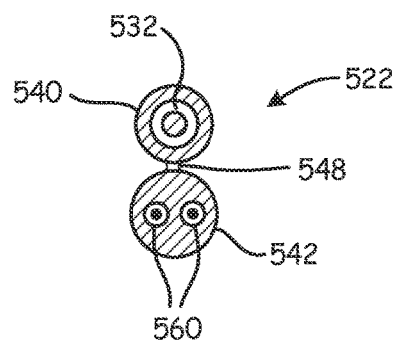
FIG. 5 is a schematic cross-sectional illustration of the leads of FIGS. 1-4 according to an exemplary embodiment.

FIG. 5 is a partial cross-section illustration of a lead body 522 usable for the various implantable leads 112, 212, 312 described therein. The lead body 522 includes a first tubular member 540 defining a stylet lumen 532 and a second tubular member 542 defining a pair of conductor lumens 560. As shown in FIG. 5, the first tubular member 540 and the second tubular member 542 are arranged in a side-by-side arrangement. The first tubular member 540 and the second tubular member 542 can be separated at a separable interface 548.

Figure 6:
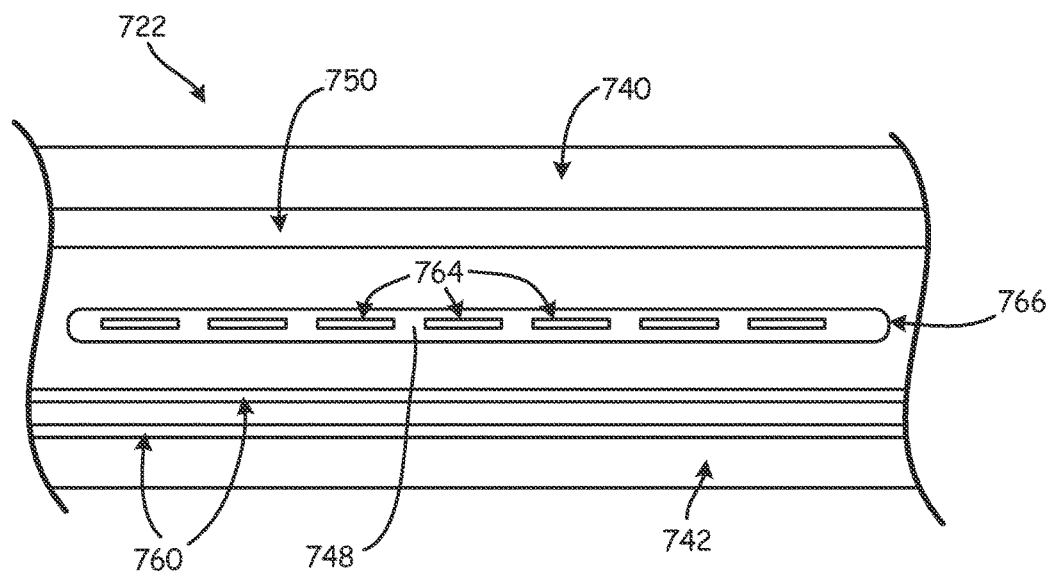
FIG. 6 is a partial schematic illustration of a lead body for the leads of FIGS. 1-4 according to an exemplary embodiment.

FIG. 6 is a schematic illustration of a lead body 722 showing in greater detail a separable interface 748 for use in one of the exemplary lead bodies as described herein. As shown, the lead body 722 has a first tubular member 740 and a second tubular member 742 coupled to one another by the separable interface 748. As further shown, the first tubular member 740 defines a stylet lumen 750 extending therethrough, and the second tubular member defines a pair of conductor lumens 760 extending therethrough. As further shown, the separable interface 748 may include holes or perforations 764 present along an entire length of the separable interface 748 creating a tear line 766. The perforations 764 may allow an operator to tear the first tubular member 740 from the second tubular member 742 along the tear line 766 without applying significant amount of pressure.

In some embodiments, the separable interface 748 may be formed by coupling the first tubular member 740 and the second tubular member 742 along their longitudinal length. Coupling can be achieved by heat bonding, stamping, or the like. Techniques known in the art such as puncturing, hot pin perforation, cold pin perforation, crimping, or the like may be used to form the perforations 764. In other embodiments, a single tubular structure including the first and second tubular members 740, 742 may be formed using molding or extrusion techniques.

In some embodiments, the separable interface 748 may be made continuous with the first tubular member 740 and the second tubular member 742 e.g., a monolithically formed unitary structure. In other embodiments, the separable interface 748 can be discrete and coupled to the first tubular member 740 and the second tubular member 742. The separable interface 748 can be formed using a suitable material such as polyethylene, silicone, polyurethane, or the like.

According to an exemplary embodiment, a method of implanting an implantable lead (e.g., the implantable leads 112, 212, 312) is described herein. During operation, the implantable lead is inserted through a small incision formed in the skin of the neck to expose the carotid sinus. The lead includes a lead body, which in turn includes the stylet lumen configured to receive a stylet and a conductor lumen configured to enclose one or more conductors. A stylet is then inserted into a stylet lumen of a lead body. The stylet is sized and shaped to be received within the stylet lumen, and further includes a bend defining a distal portion of the stylet having a predetermined angle of incidence relative to a proximal portion of the stylet proximal to the bend. Once the stylet is disposed in the stylet lumen, an electrode coupled to the conductor at a distal end of the conductor is positioned proximate to a target physiological region of a patient. This can be achieved by using the stylet to stiffen and support the lead body.

In some embodiments, the method further includes rotating the stylet to expose a temporary attaching element. As a next step, the temporary attaching element is engaged with patient tissue without affecting response of baroreceptors. This provides an advantage of securing the lead to the target physiological region so as to stabilize the lead for the time required to accurately map the target region. Once the location for treatment is found, the electrode can be secured to the patient by any suitable technique such as, suturing, clipping, stapling, or the like. Upon securing or fixation of the electrode, the stylet can be removed from the medical apparatus.

In some embodiments, removing the stylet from the medical apparatus includes removing a first tubular member that defines the stylet lumen from the medical apparatus. The first tubular member is separated from the medical apparatus by pulling the first tubular member away from the medical apparatus thereby, tearing the first tubular member. The first tubular member can be torn along a separable interface. While removing the first tubular member from the medical apparatus, the stylet may remain within the stylet lumen.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical apparatus, comprising:
    an implantable lead for stimulation of a target region of a patient's nervous system, the lead comprising:
        a generally tubular lead body having a proximal end, an opposite distal end, a stylet lumen and a conductor lumen, the stylet and conductor lumens extending through the proximal and distal ends of the tubular lead body;
        a conductor enclosed within the conductor lumen;
        an electrode assembly extending from the distal end of the lead body, the electrode assembly including a flexible polymeric carrier, and an electrode on the carrier and electrically coupled to the conductor; and
        a stylet sized and shaped to be receivable within the stylet lumen and configured to stiffen and support the lead body, wherein the stylet includes a proximal portion and a distal portion, wherein a temporary anchoring element is coupled to a distal end of the distal portion of the stylet, wherein the temporary anchoring element is configured to extend from, and retract into, the distal end of the stylet.

2. The medical apparatus of claim 1, wherein the lead body includes a first tubular member and a second tubular member secured to the first tubular member, the stylet lumen extending through the first tubular member, wherein the first tubular member is separable from the second tubular member.

3. The medical apparatus of claim 1, wherein the lead body further comprises a separable interface between the first tubular member and the second tubular member, wherein the stylet is detachable from the lead body at the separable interface by removing the first tubular member along the separable interface.

4. The medical apparatus of claim 1, wherein the temporary anchoring element comprises a barb configured to pierce patient tissue in order to engage with the patient tissue.

5. The medical apparatus of claim 4, wherein the barb comprises a tip portion configured to engage with the patient tissue.

6. The medical apparatus of claim 4, wherein the temporary anchoring element comprises a fixation helix with a sharp tip portion that is configured to be extendable from and retractable with respect to the distal end of the stylet when the stylet is rotated relative to the lead body.

7. The medical apparatus of claim 1, wherein the conductor lumen and the stylet lumen are situated in a side-by-side arrangement.

8. The medical apparatus of claim 1, further comprising a second conductor enclosed within a second conductor lumen.

9. The medical apparatus of claim 8, further comprising a second electrode electrically coupled to the second conductor.

10. The medical apparatus of claim 9, wherein the lead body includes a first tubular member, the stylet lumen extending through the first tubular member, wherein the first tubular member has a circular opening at a distal end of the first tubular member and wherein the stylet is configured to extend past and retract into the first tubular member through the circular opening.

11. The medical apparatus of claim 1, wherein the carrier is composed of a silicone-based material.

12. A method of implanting an implantable lead for stimulation of the baroreceptors located within a carotid sinus of a patient, the method comprising:
    advancing a stylet into a stylet lumen of a lead body of the implantable lead, the lead body comprising the stylet lumen and a conductor lumen, wherein a conductor is enclosed within the conductor lumen, and wherein the stylet is sized and shaped to be receivable within the stylet lumen, wherein the stylet is configured to stiffen and support the lead body and includes a proximal portion and a distal portion, wherein a temporary anchoring element is coupled to a distal end of the distal portion, and wherein the temporary anchoring element is configured to extend from, and retract into, the distal end of the stylet; and
    positioning an electrode of the implantable lead proximate to a target physiological region of a patient by using the stylet to stiffen and support the lead body, wherein the electrode is electrically coupled to the conductor at a distal end of the conductor.

13. The method of claim 12, further comprising rotating the stylet to expose the temporary anchoring element.

14. The method of claim 13, further comprising engaging the temporary anchoring element with patient tissue.

15. The method of claim 14, further comprising:
    securing the electrode to the patient; and
    removing the stylet from the medical apparatus upon securing the electrode to the patient.

16. The method of claim 15, wherein removing the stylet from the medical apparatus comprises removing a first tubular member defining the stylet lumen from the medical apparatus, wherein the stylet remains enclosed within the first tubular member while removing the first tubular member.

* * * * *